United States Patent [19]

Teach

[11] 4,219,655
[45] Aug. 26, 1980

[54] PROCESS FOR THE PRODUCTION OF N-ACYL SUBSTITUTED OXAZOLIDINES

[75] Inventor: Eugene G. Teach, El Cerrito, Calif.

[73] Assignee: Stauffer Chemical Company, Westport, Conn.

[21] Appl. No.: 57,614

[22] Filed: Jul. 16, 1979

[51] Int. Cl.$^2$ ............................................. C07D 263/08
[52] U.S. Cl. ..................................................... 548/215
[58] Field of Search ........................................ 548/215

[56] References Cited

U.S. PATENT DOCUMENTS

| | | | |
|---|---|---|---|
| 3,707,541 | 12/1972 | Lajiness | 548/215 |
| 4,072,688 | 2/1978 | Teach | 548/215 |
| 4,137,070 | 1/1979 | Pallos et al. | 71/100 |

Primary Examiner—Jose Tovar
Attorney, Agent, or Firm—Joel G. Ackerman

[57] ABSTRACT

N-acyl substituted oxazolidines having the formula

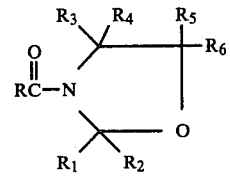

in which R is $C_1$–$C_6$ haloalkyl, $C_1$–$C_6$ alkyl, $C_1$–$C_6$ thioalkyl or $C_2$–$C_4$ haloalkenyl; $R_1$ is hydrogen, $C_1$–$C_6$ alkyl, phenyl or substituted phenyl, $R_2$, $R_3$, $R_4$ and $R_6$ are independently hydrogen or $C_1$–$C_4$ alkyl and $R_5$ is hydrogen, $C_1$–$C_4$ alkyl or phenyl, are prepared by the reaction of a 2-hydroxyethylamide having the formula

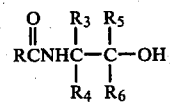

with an acetal or ketal having the formula

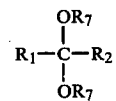

in which $R_7$ is $C_1$–$C_4$ alkyl, in the presence of an acid catalyst.

7 Claims, No Drawings

PROCESS FOR THE PRODUCTION OF N-ACYL SUBSTITUTED OXAZOLIDINES

BACKGROUND OF THE INVENTION

This application relates to the production of N-acyl substituted oxazolidines. Such compounds are described in a number of patents, including for example, U.S. Pat. Nos. 3,707,541, 3,959,304, 3,989,503, 4,072,688 and 4,137,070. Such compounds in general have the formula

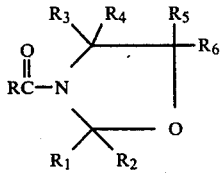

in which R can be variously alkyl, haloalkyl, thioalkyl or haloalkenyl, $R_1$ can be hydrogen, alkenyl, phenyl or substituted phenyl, $R_2$, $R_3$ and $R_4$ hydrogen or alkyl, $R_5$ hydrogen, alkyl or phenyl and $R_6$ hydrogen or alkyl. As described in these and other patents and publications, such compounds may find use as herbicides and/or herbicidal antidotes, the latter in combination with various types of herbicides.

In general, the process for the production of such compounds as given in those patents involved the reaction of an alkanolamine having the formula

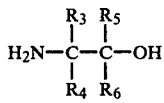

with a carbonyl compound having the formula

to produce an oxazolidine followed by acylation using a compound having the formula RCOX, in which X is a halogen. (R-$R_6$ being defined as above). Additionally, U.S. Pat. No. 4,038,284 describes an improvement in conducting such a process in which the acylation step is conducted in the presence of water.

SUMMARY OF THE INVENTION

This invention provides a new process for producing N-acylated oxazolidines, comprising the reaction between a substituted 2-hydroxyethylamide and an acetal or ketal, producing the N-acylated oxazolidine and an alcohol.

More particularly, this invention relates to the production of compounds having the formula

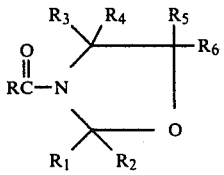

in which R is $C_1$-$C_6$ haloalkyl, $C_1$-$C_6$ alkyl, $C_1$-$C_6$ thioalkyl, or $C_2$-$C_4$ haloalkenyl, $R_1$ is hydrogen, $C_1$-$C_6$ alkyl, phenyl or substituted phenyl in which the substituents are mono or dichloro, nitro, methyl, methoxy or hydroxy, $R_2$, $R_3$, $R_4$ and $R_6$ are hydrogen or $C_1$-$C_4$ alkyl and $R_5$ is hydrogen, $C_1$-$C_4$ alkyl or phenyl, in which a 2-hydroxyethylamide having the formula

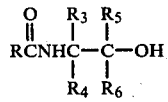

is reacted with an acetal or ketal having the formula

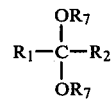

in which $R_7$ is $C_1$-$C_4$ alkyl, in the presence of an acid catalyst. (When $R_1$ or $R_2$ is hydrogen, the compound is an acetal; when both are alkyl it is a ketal).

The general reaction for this process is:

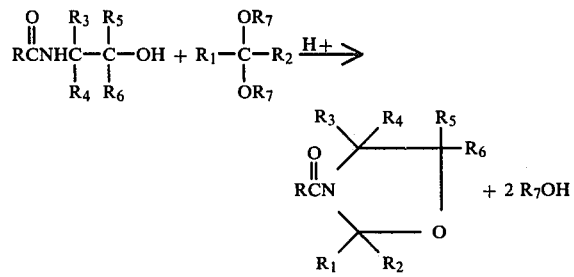

The terms "halo-alkyl and halo-alkenyl" are meant to include such groups containing chloro and/or bromo substituents and which may be mono-, di-, tri-, tetra- and/or per-substituted.

A preferred class of oxazolidines produced by this process are those in which R is $C_1$-$C_4$ haloalkyl, $R_1$, $R_2$, $R_3$, $R_4$ and $R_6$ are hydrogen or $C_1$-$C_4$ alkyl and $R_5$ is hydrogen, $C_1$-$C_4$ alkyl or phenyl. A particularly preferred class of compounds of this type is one in which $R_1$ and $R_2$ are $C_1$-$C_4$ alkyl, $R_3$, $R_4$ and $R_6$ are hydrogen and $R_5$ is hydrogen, lower alkyl or phenyl. Examples of particularly preferred compounds are: 2,2-dimethyl-3-dichloroacetyl-1,3-oxazolidine; 2,2,5-trimethyl-3-dichloroacetyl-1,3-oxazolidine; 2,2-dimethyl-3-dichloroacetyl-5-n-propyl-1,3-oxazolidine; and 2,2-dimethyl-3-dichloroacetyl-5-phenyl-1,3-oxazolidine.

The following represents an example of the process, in this case, for the preparation of 2,2-dimethyl-3-dichloroacetyl-5-phenyl-1,3-oxazolidine.

In 100 milliliters benzene was suspended 24.8 grams of N-2-phenyl-2-hydroxyethyl dichloroacetamide. There was then added 11 grams of 2,2-dimethoxypropane and about 300 milligrams of p-toluenesulfonic acid. The mixture was heated to reflux in a distillation column and the benzene-methanol azeotrope boiling at 57° C. was removed. When the head temperature of the column had risen to 80° C. the flask was cooled and the benzene stripped, with 27 grams of product being recovered. A sample of the product was recrystallized from ether to give a material having a melting point of 98°–102° C. The product was analyzed by infrared (ir) and nuclear magnetic resonance (nmr) spectroscopy.

According to this invention, the reaction of the 2-hydroxyethylamide with an acetal or ketal may be conducted at a temperature within the range of from about 60° C. to about 110° C., preferably from about 80° C. to about 110° C., and at pressures within the range of from about 0.5 to about 3 atm. abs. In addition to benzene, other solvents may be utilized, for example toluene, n-hexane, n-heptane and n-octane. If necessary, the product of the reaction may be purified by use of any of the conventional methods for purification of such oxazolidines. In addition to the p-toluenesulfonic acid utilized in the example, other suitable acid catalysts are boron trifluoride etherate, sulfuric acid and naphthalenesulfonic acid.

What is claimed is:

1. A process for the production of an N-acyl substituted oxazolidine having the formula

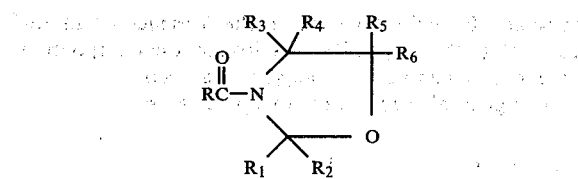

in which R is $C_1$–$C_6$ haloalkyl, $C_1$–$C_6$ alkyl, $C_1$–$C_6$ thioalkyl or $C_2$–$C_4$ haloalkenyl, $R_1$ is hydrogen, $C_1$–$C_6$ alkyl, phenyl or substituted phenyl in which the substituents are mono- or di-chloro, nitro, methyl, methoxy or hydroxyl; $R_2$, $R_3$, $R_4$ and $R_6$ are independently hydrogen or $C_1$–$C_4$ alkyl and $R_5$ is hydrogen, $C_1$–$C_4$ alkyl or phenyl, comprising reacting a compound having the formula

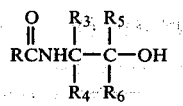

in which R, $R_3$, $R_4$, $R_5$ and $R_6$ are as defined above, with a compound having the formula

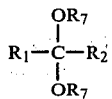

in which $R_1$ and $R_2$ are as defined above and $R_7$ is $C_1$–$C_4$ alkyl, in the presence of an acid catalyst.

2. A process according to claim 1 in which R is $C_1$–$C_4$ halo-alkyl, $R_1$, $R_2$, $R_3$, $R_4$ and $R_6$ are independently hydrogen or $C_1$–$C_4$ alkyl and $R_5$ is hydrogen, $C_1$–$C_4$ alkyl or phenyl.

3. A process according to claim 2 in which $R_1$ and $R_2$ are $C_1$–$C_4$ alkyl and $R_3$, $R_4$ and $R_6$ are each hydrogen.

4. A process according to claim 1 in which both $R_7$ groups are methyl.

5. A process according to claim 1 in which the temperature is from about 60° C. to about 110° C.

6. A process according to claim 5 in which the temperature is from about 80° C. to about 110° C.

7. A process according to claim 1 in which the acid catalyst is p-toluenesulfonic acid.

* * * * *